United States Patent
Hong et al.

(10) Patent No.: US 10,239,866 B2
(45) Date of Patent: Mar. 26, 2019

(54) SELECTIVE METHODS FOR THE SEPARATION OF ONDANSETRON AND RELATED IMPURITIES

(71) Applicant: Waters Technologies Corporation, Milford, MA (US)

(72) Inventors: Paula Hong, Ashland, MA (US); Jennifer Simeone, Shrewsbury, MA (US)

(73) Assignee: Waters Technologies Corporation, Milford, MA (US)

( * ) Notice: Subject to any disclaimer, the term of this patent is extended or adjusted under 35 U.S.C. 154(b) by 17 days.

(21) Appl. No.: 15/404,309

(22) Filed: Jan. 12, 2017

(65) Prior Publication Data

US 2017/0197942 A1    Jul. 13, 2017

Related U.S. Application Data

(60) Provisional application No. 62/359,345, filed on Jul. 7, 2016, provisional application No. 62/277,660, filed on Jan. 12, 2016.

(51) Int. Cl.
| | |
|---|---|
| *C07D 403/08* | (2006.01) |
| *B01D 15/42* | (2006.01) |
| *B01J 20/26* | (2006.01) |
| *B01J 20/28* | (2006.01) |
| *B01J 20/285* | (2006.01) |

(52) U.S. Cl.
CPC ......... *C07D 403/08* (2013.01); *B01D 15/426* (2013.01); *B01J 20/265* (2013.01); *B01J 20/28004* (2013.01); *B01J 20/285* (2013.01); *B01J 20/28019* (2013.01); *B01J 20/28061* (2013.01); *B01J 20/28083* (2013.01); *B01J 2220/46* (2013.01); *B01J 2220/52* (2013.01)

(58) Field of Classification Search
None
See application file for complete search history.

(56) References Cited

PUBLICATIONS

"Ondansetron Orally DisintegratingTablets," The United States Pharamaoperial Convention, Revision Bulletin, (Dec. 2010).
"Ondansetron Tablets," The United States Pharamaoperial Convention, Revision Bulletin, (Mar. 2010).
"USP Standards: Monographs (Written Standards)," U.S. Pharmacopeia Fact Sheet, (2008).
Hong, et al., "Transfer of an HPLC Method from an Agilent 1100 Series LC System to an Alliance HPLC System," Waters Corporation Technology Brief (Jul. 2015).
Imran, et al., "Development and Validation of Reverse-Phase HPLC Method for Estimation of Ondansetron Hydrochloride in Bulk Drug," IRJP, vol. 3(2) Research Article (2012).
MHRA PAR, Ondansetron 4mg & 8mg Tablets PL 04543/0509-10, (2006).
Molcan Category Products: "Ondansetron" search results: http://www.molcan.com/category/1067, Molcan Corporation, 3 Pages (2014).
Roemling, et al. "HILIC-MS—High Resolution and Sensitivity for the Analysis of Very Polar Compounds," LC/GC chromatographyonline.com, (Dec. 2, 2007).
Souri, et al., "Validating a Stability Indicating HPLC Method for Kinetic Study of Ondansetron Degradation in Acidic, Basic and Oxidative Conditions," RJPBCS, pp. 51-62, (May-Jun. 2014).
Varvara, et al. "The Liquid Chromatographic Assay of Ondansetron Hydrochloride and Its Impurities Using a New Stationary Phase," Farmacia, vol. LVI, 2, pp. 154-165, (2008).
Varvara, et al., "ION-PAIR Reversed-Phase High Performance Liquid Chromatography of Ondansetron Hydrochloride Using Sodium Heptanesulphonate as a Counterion," Farmacia, vol. 57:4, pp. 442-452 (2009).
"Ondanestron," USP 31, Official Monographs, p. 1, (2008).

*Primary Examiner* — Samantha L Shterengarts
(74) *Attorney, Agent, or Firm* — Womble Bond Dickinson (US) LLP; Deborah M. Vernon; Rebecca N. Barnes (57) ABSTRACT

The present disclosure generally relates to methods for separating ondansetron and related impurities using $CO_2$-based chromatography.

14 Claims, 6 Drawing Sheets

SELECTIVE METHODS FOR THE SEPARATION OF ONDANSETRON AND RELATED IMPURITIES

REFERENCE TO RELATED APPLICATIONS

This application claims priority to U.S. Provisional Application No. 62/277,660, filed Jan. 12, 2016 and U.S. Provisional Application No. 62/359,345, filed Jul. 7, 2016, each of which are incorporated herein by reference.

TECHNICAL FIELD

The present disclosure generally relates to methods for separating ondansetron and related impurities using $CO_2$-based chromatography.

BACKGROUND

Quality control of drug substances is an essential feature in the global marketplace to support public health and safety. To ensure compliance, regulatory bodies such as the U.S. Food and Drug Administration (FDA), typically monitor and hold pharmaceutical companies to certain standards. One important standard that is imposed on pharmaceutical companies by the FDA is the use of protocols described in the United States Pharmacopeia (USP).

USP establishes documentary standards in the form of monographs to establish product safety, sterility, strength, quality, purity and overall consistency. Monographs typically include the name of the ingredient or preparation, the definition, packaging, storage, label requirements, and the specification. The specification consists of a series of tests, procedures for the tests, and acceptance criteria, to which medicinal ingredients and products will have the stipulated strength, quality, and purity if conformance to the requirements in the monograph is met.

Ondansetron is a serotonin 5-HT3 receptor antagonist used to prevent nausea and vomiting that may be caused by medicines or radiation therapy. In addition to its therapeutic properties, ondansetron is particularly interesting from an analytical standpoint because, while monographs for quantitative determination of ondansetron provide strict limits on purity, separating ondansetron from its also highly polar related impurities, particularly 2-methylimidazole and imidazole, is challenging. For example, the difference in retention time between Impurity C and Impurity D from the reverse phase High Performance Liquid Chromatography (HPLC) set forth in the USP monograph is only two one hundredths of a second (0.02 seconds) difference. See e.g., USP monograph. Yet, the total combined limit for these impurities is 0.3%. Similarly, there is only five one hundredths of a second (0.05 seconds) difference in retention time between 2-methylimidazole and imidazole, and only a tenth of a second difference in retention time between ondansetron and impurity A. See id. Yet, the total combined limit for these impurities is 0.6%.

Because strict compliance with these mandated impurity limits is necessary to support the safe use of ondansetron, one problem has been how to identify and effectively separate ondansetron and its impurities from a sample in a reproducible manner that is suitable for high throughput quality control analysis. Several methods have been attempted, but require the use of ion-pairing, utilize more elaborate column materials (e.g., non-traditional silica bonded phases such as zirconium oxide or porous graphitic carbon), are not compatible with mass spectrometry, utilize high buffer concentrations and long equilibration times, or do not optimally separate the ondansetron impurities. See e.g., Research Journal of Pharmaceutical, Biological and Chemical Sciences, May-June 2014, 5(3) Pages 51-62; Alam Imran et al., International Research Journal of Pharmacy 2012, 3(2), pages 111-113; and Roemling et al., TOSOH Bioscience Application Note A08L16A.

Given the importance of quality control of drug substances in the marketplace, the need remains to develop a reliable high-throughput method for optimally separating the highly polar anti-nausea and anti-vomiting therapeutic ondansetron and its related impurities.

SUMMARY

In general, the present disclosure relates to robust, high-throughput, and industrially applicable methods for separating ondansetron and related impurities using $CO_2$-based chromatography.

Figure 3:
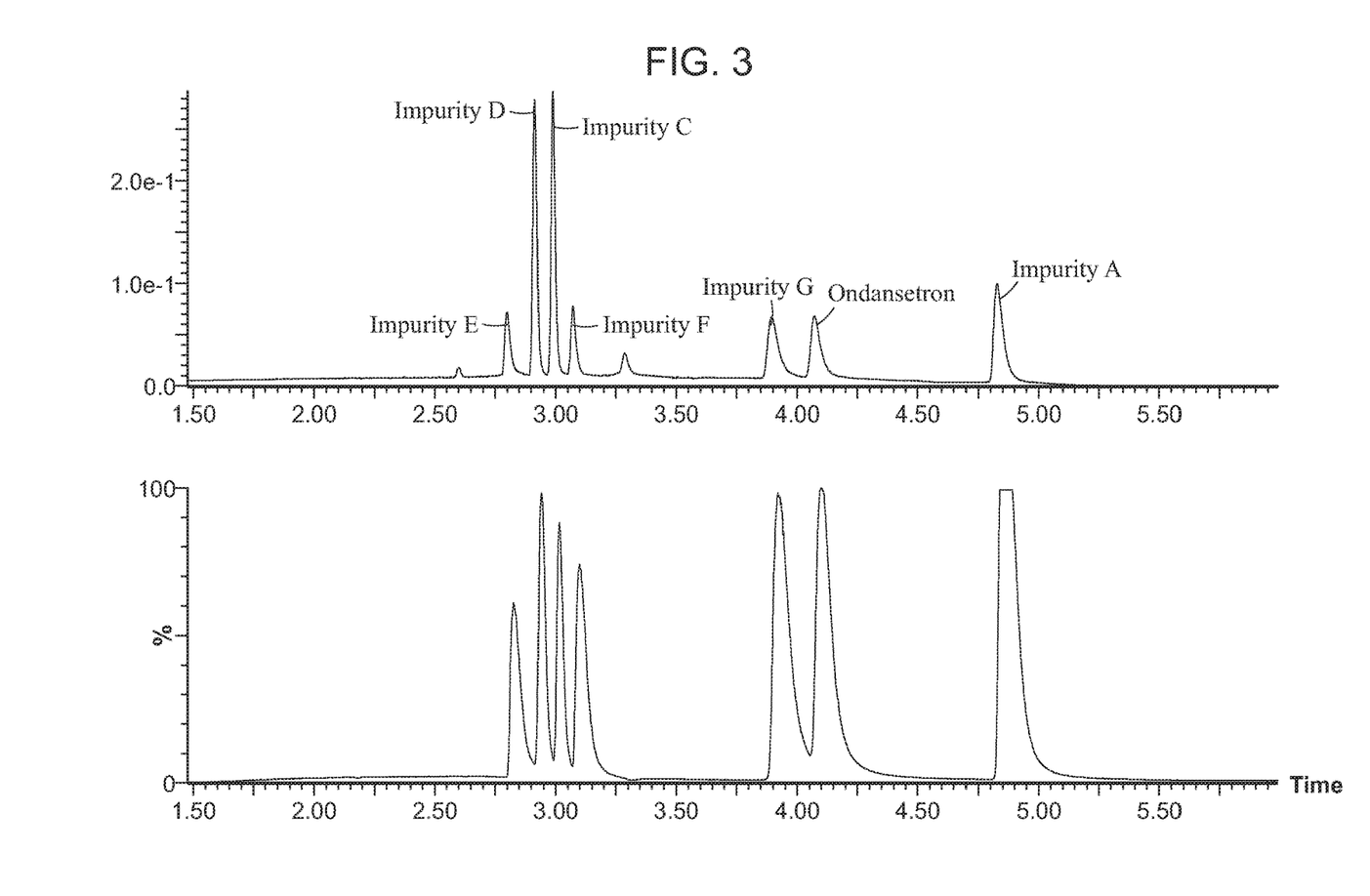
FIG. 3 depicts a chromatogram of the separation of ondansetron and related impurities using a fluorophenyl based chromatography column following the $CO_2$-based chromatography methods described herein.

The disclosed methods provide orthogonal selectivity in which highly polar related impurities of ondansetron are easily retained (e.g., elution time of the first related impurity is 1.5 minutes or greater) on commercially available chromatography columns. See e.g., FIG. 3 and FIG. 4.

In addition, the methods described herein allow for reduced solvent consumption, shorter analysis time (e.g., a total run time of 6.0 minutes or less), and alternate selectivity (e.g., by changing column chemistries), and do not require pre-column derivitization steps or the use of ion-paring reagents, high buffer concentrations, or long equilibration times, each of which ultimately lead to, in one aspect, a reliable high-throughput method for optimally separating ondansetron and related impurities for quality control industrial analyses.

DETAILED DESCRIPTION OF CERTAIN EMBODIMENTS

In a first exemplary embodiment, provided are methods of separating ondansetron and at least one related impurity using $CO_2$-based chromatography, comprising applying a sample of ondansetron and at least one related impurity to a chromatography column; and eluting ondansetron and the at least one related impurity from the chromatography column using a mobile phase comprising CO₂.

Ondansetron (mw=293.4) refers to the serotonin 5-HT₃ receptor antagonist having the structure:

or a salt or hydrate thereof.

Related impurities of ondansetron refer to any one of the following compounds:

Impurity A: 3-((dimethylamino)methyl)-9-methyl-2,3-dihydro-1H-fluoren-4(9H)-one, (mw=256.3), having the structure:

or a salt or hydrate thereof.

Impurity B: 6,6'-methylenebis(9-methyl-3-((2-methyl-1H-imidazol-1-yl)methyl)-2,3-dihydro-1H-fluoren-4(9H)-one), (mw=598.7), having the structure:

or a salt or hydrate thereof.

Impurity C: 9-methyl-2,3-dihydro-1H-fluoren-4(9H)-one, (mw=199.25), having the structure:

or a salt or hydrate thereof.

Impurity D: 9-methyl-3-methylene-2,3-dihydro-1H-fluoren-4(9H)-one, (mw=199.3) having the structure:

or a salt or hydrate thereof.

Impurity E: imidazole, (mw=68.1), having the structure:

or a salt or hydrate thereof.

Impurity F: 2-methylimidazole, (mw=82.1), having the structure:

or a salt or hydrate thereof.

Impurity G: 3-((1H-imidazol-1-yl)methyl)-9-methyl-2,3-dihydro-1H-fluoren-4(9H)-one, (mw=279.3), having the structure:

or a salt or hydrate thereof.

Impurity H: 3-((2-methyl-1H-imidazol-1-yl)methyl)-2,3-dihydro-1H-fluoren-4(9H)-one, (mw=279.3), having the structure:

or a salt or hydrate thereof.

Related impurities may be attributed with or contained in a single sample of ondansetron (e.g., as part of a pharmaceutical composition such as enteral, topical, and parenteral) thorough naturally occurring degradation processes, or may be introduced externally as foreign components to an otherwise related impurity-free form of ondansetron. For example, related impurities of ondansetron cover instances where a pure or related impurity-free form of ondansetron is received from a manufacture and related impurities are then introduced to the sample from external sources (e.g., through human intervention, processes, and the like), and in instances where a form of ondansetron is received from a manufacture and it already contains related impurities (e.g., through natural degradation or from impure techniques or lack of quality control).

The $CO_2$ in the methods described herein (e.g., in the mobile phase) can be in one or more physical states. For example, in one aspect, the $CO_2$ is in liquid form. In another aspect, the $CO_2$ is a supercritical liquid or subcritical liquid state, or both.

Due to its miscibility, the $CO_2$ mobile phase can be combined with one or more modifiers (co-solvents) to improve desorption or elution of the ondansetron and at least one related impurity described herein. Thus, in a second exemplary embodiment, the mobile phase comprising $CO_2$ in the methods described herein further comprises a modifier. Suitable modifiers include e.g., polar water-miscible organic solvents, such as methanol, ethanol, isopropanol, acetonitrile, acetone, and tetrahydrofuran, or mixtures of water and any of these solvents. Additional features are described herein such as e.g., those described in the first exemplary embodiment. Optimal amounts of modifiers, mixtures thereof, as well as the amounts and gradients of $CO_2$ and modifiers used in the separation methods depends upon e.g., the sample and column features, and would be apparent to one of skill in the art.

In a third exemplary embodiment, the related impurities described herein are Impurity E and Impurity F collectively. Thus, one aspect includes a method of separating ondansetron and both Impurity E and Impurity F using $CO_2$-based chromatography, comprising applying a sample of ondansetron and Impurity E and Impurity F to a chromatography column; and eluting ondansetron and Impurity E and Impurity F from the chromatography column using a mobile phase comprising $CO_2$. Additional features are described herein such as e.g., those described in the first and second exemplary embodiments.

In a fourth exemplary embodiment, the related impurities described in the methods herein are Impurity E and Impurity F collectively, wherein Impurity E and Impurity F have a retention time difference of greater than 10 seconds apart from one another. Additional features are described herein such as e.g., those described in the first, second, and third exemplary embodiments.

In a fifth exemplary embodiment, the related impurities described in the methods herein are Impurity A, Impurity C, Impurity D, Impurity E, Impurity F, and Impurity G collectively. Additional features are described herein such as e.g., those described in the first, second, third, and fourth exemplary embodiments.

In a sixth exemplary embodiment, the related impurities described in the methods herein are Impurity A, Impurity B, Impurity C, Impurity D, Impurity E, Impurity F, Impurity G, and Impurity H collectively. Additional features are described herein such as e.g., those described in the first, second, third, fourth, and fifth exemplary embodiments.

In a seventh exemplary embodiment, the retention time of the first related impurity eluted from the chromatography column is greater than 1.5 minutes. For example, in the case where all related impurities are present (i.e., Impurity A, Impurity B, Impurity C, Impurity D, Impurity E, Impurity F, Impurity G, and Impurity H, collectively), if Impurity C was the first impurity to elute, then the retention time of Impurity C is not to be 1.5 minutes or less. Additional features are described herein such as e.g., those described in the first, second, third, fourth, fifth, and sixth exemplary embodiments.

In an eighth exemplary embodiment, the total elution period of the ondansetron and related impurities is less than 10 minutes (e.g., less than 9 minutes, less than 8 minutes, less than 7 minutes, less than 6 minutes, less than 5.5 minutes, and anytime in between). Additional features are described herein such as e.g., those described in the first, second, third, fourth, fifth, sixth, and seventh exemplary embodiments. As used herein, total elution period is the time at which the last related impurity of ondansetron has eluted from the chromatography column, or the time by which ondansetron has eluted from the chromatography column if all related impurities eluted prior to ondansetron. Total elution period may also be identified as the total run time.

The $CO_2$-based System and Method of Use $CO_2$-based chromatography systems, as well as related components, that can be used in the present methods are described in e.g., U.S. Patent Application Publication Nos. 2015/0331001 and 2014/0157871 and International Application Publication Nos. WO 2013/134468, WO 2013/134473, WO 2013/134471, WO 2013/134476, WO 2013/134475, WO 2013/134485, WO 2013/134483, WO 2013/134478, and WO 2013/134496, each of which are incorporated herein by reference.

Figure 1:
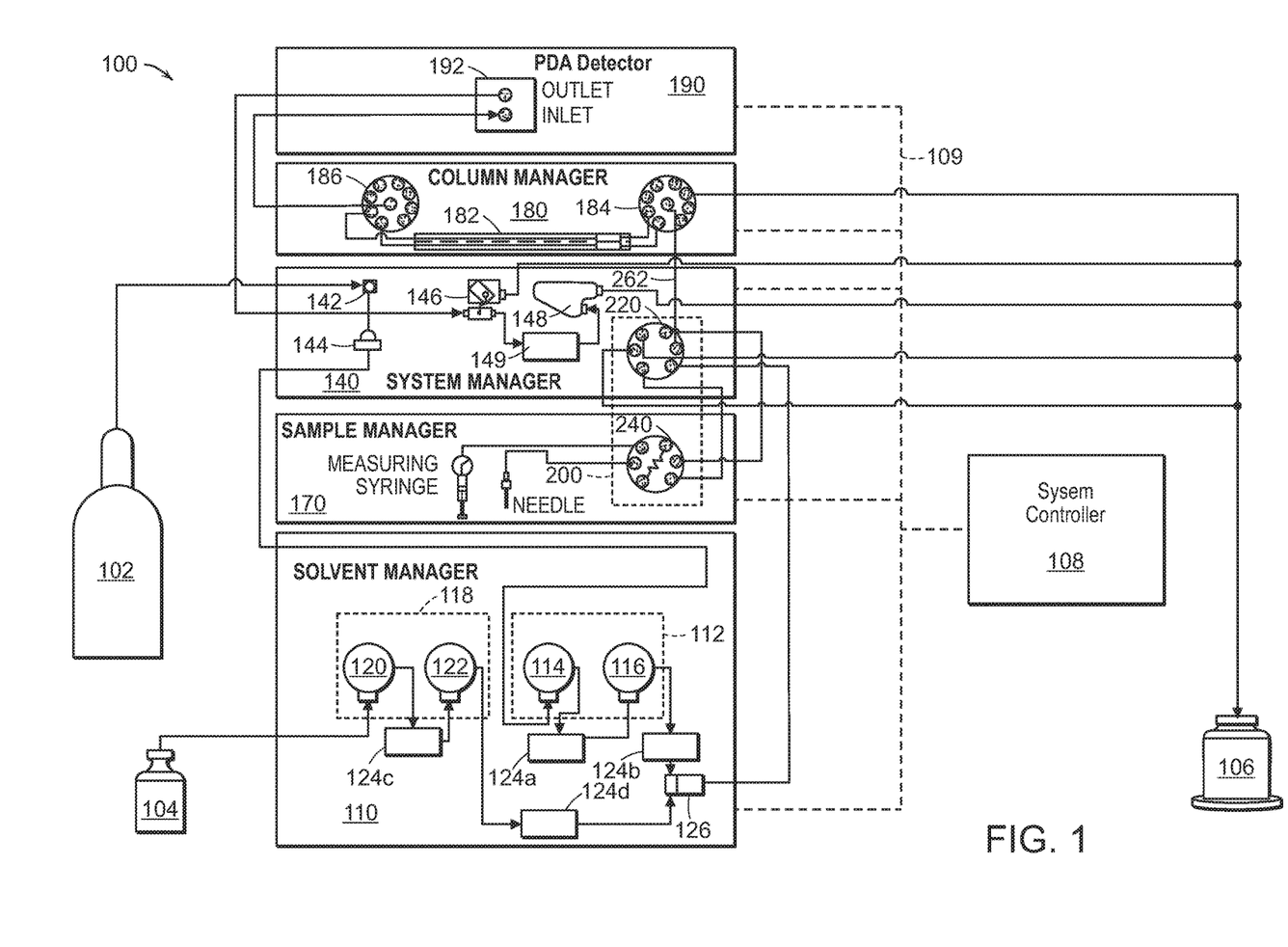
FIG. 1 is a schematic view of an exemplary $CO_2$-based chromatography system for use in the methods described herein.

For example, FIG. 1 illustrates an exemplary and basic diagram of a $CO_2$ based system from the above disclosures, and which can be used to facilitate the methods described herein. As depicted, the $CO_2$ based system 100 comprises a plurality of stackable modules including a solvent manager 110; a system manager 150; a sample manager 170; a column manager 180; and a detector module 190.

By way of illustration, the solvent manager 110 is comprised of a first pump 112 which receives carbon dioxide from $CO_2$ source 102 (e.g., a tank containing compressed $CO_2$). The $CO_2$ passes through an inlet shutoff valve 142 and a filter 144 in the system manager 140 on its way to the first pump 112. The first pump 112 can comprise one or more actuators each comprising or connected to cooling means, such as a cooling coil and/or a thermoelectric cooler, for cooling the flow of $CO_2$ as it passes through the first pump 112 to help ensure that the $CO_2$ fluid flow is deliverable in e.g., liquid form. In some cases, the first pump 112 comprises a primary actuator 114 and an accumulator actuator 116. The primary and accumulator actuators 114, 116 each include an associated pump head, and are connected in series. The accumulator actuator 116 delivers $CO_2$ to the system 100. The primary actuator 114 delivers $CO_2$ to the system 100 while refilling the accumulator actuator 116.

Also by way of illustration, the solvent manager 110 also includes a second pump 118 for receiving an organic co-solvent (e.g., methanol, etc.) from a co-solvent source 104 and delivering it to the system 110. The second pump 118 can comprise a primary actuator 120 and an accumulator actuator 122, each including an associated pump head. The primary and accumulator actuators 120, 122 of the second pump 118 are connected in series. The accumulator actuator 122 delivers co-solvent to the system 100. The primary actuator 120 delivers co-solvent to the system 100 while refilling the accumulator actuator 122.

Also by way of illustration, transducers 124*a-d* are connected to outlets of the respective pump heads for monitoring pressure. The solvent manager 110 also includes electrical drives for driving the primary actuators 114, 120 and the accumulator actuators 116, 122. The $CO_2$ and co-solvent fluid flows are mixed at a tee 126 forming a mobile phase fluid flow that continues to an injection valve subsystem 200, which injects a sample slug for separation into the mobile phase fluid flow.

Also by way of illustration, the injection valve subsystem 200 is comprised of an auxiliary valve 220 that is disposed in the system manager 140 and an inject valve 240 that is disposed in the sample manager 170. The auxiliary valve 220 and the inject valve 240 are fluidically connected and the operations of these two valves are coordinated in such a manner as to reduce sample carryover and system pressure perturbations occurring during injection. The reduced system pressure perturbations eliminate back flow in the column that may occur during injection and as the result of system pressure drops. The system manager 140 includes a valve actuator for actuating the auxiliary valve 220 and electrical drives for driving the valve actuations. Similarly, the sample manager 170 includes a valve actuator for actuating the inject valve and electrical drives for driving the valve actuations.

Also by way of illustration, from the injection valve subsystem 200, the mobile phase flow containing the injected sample slug continues through a separation column 182 in the column manager 180, where the sample slug is separated into its individual component parts. The column manager 180 comprises a plurality of such separation columns, and inlet and outlet switching valves 184, 186 for switching between the various separation/chromatography columns.

Also by way of illustration, after passing through the separation column 182, the mobile phase fluid flow continues on to a detector 192 (e.g., a flow cell/photodiode array type detector) housed within the detector module 190 then through a vent valve 146 and then on to a back pressure regulator 148 in the system manager 140 before being exhausted to waste 106. A transducer 149 is provided between the vent valve 146 and the back pressure regulator 148.

Also by way of illustration, the back pressure regulator 148 is adjustable to control or modify the system fluid pressure. This can allow the pressure to be changed from run to run. The properties of $CO_2$ affect how quickly compounds are extracted from the separation column 182, so the ability to change the pressure can allow for different separation based on pressure. The back pressure regulator 148 can be used to maintain the system pressure in the range of 1000 psi to 9000 psi e.g., in the range of 1000 psi to 6000 psi, or e.g., in the range of 1000 psi to 4000 psi, or at any particular pressure within these ranges.

Also by way of illustration, also shown schematically in FIG. 1 is a computerized system controller 108 that can assist in coordinating operation of the $CO_2$ based system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. Each module's control electronics can also include at least one processor for executing the computer readable instructions, receiving input, and sending output. The control electronics can also include one or more digital-to-analog (D/A) converters for converting digital output from one of the processors to an analog signal for actuating an associated one of the pumps or valves (e.g., via an associated pump or valve actuator).

The control electronics can also include one or more analog-to-digital (A/D) converters for converting an analog signal, such as from system sensors (e.g., pressure transducers), to a digital signal for input to one of the processors. Some or all of the various features of these control electronics can be integrated in a microcontroller.

Figure 2:
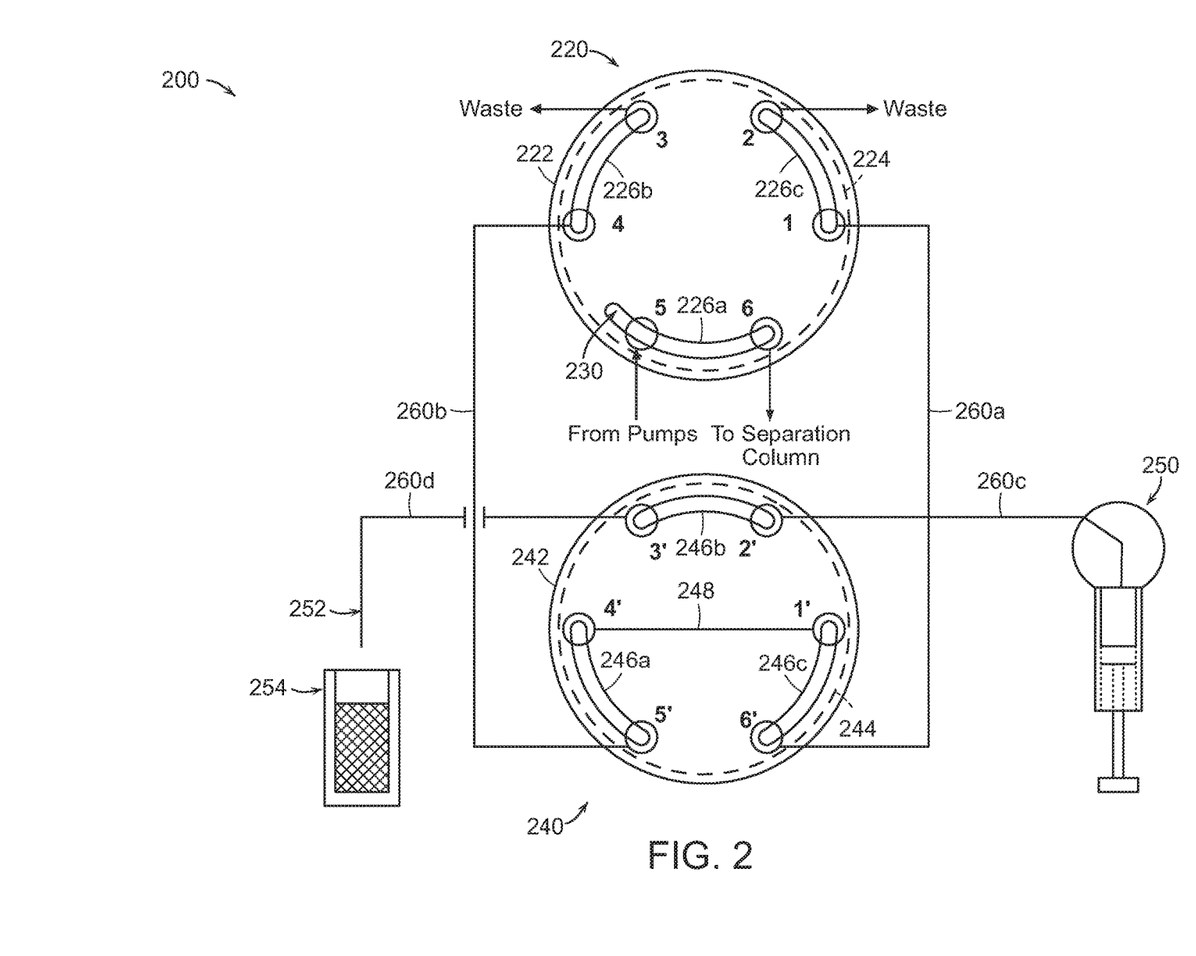
FIG. 2 is a schematic view of an exemplary injection valve for the $CO_2$-based system shown in FIG. 1.

Also by way of illustration, the injection valve subsystem 200 including the auxiliary valve 220 and the inject valve 240 is illustrated in FIG. 2. The auxiliary valve 220 is a rotary shear valve that includes an auxiliary valve stator 222 that has a plurality of ports, numbered 1 through 6 in FIG. 2, and an auxiliary valve rotor 224 that has a rotor interface, which includes three fluid conduits in the form of arcuate grooves 226*a-c*. When assembled, the rotor interface is urged into contact with the auxiliary valve stator 222, e.g., by pressure exerted on the auxiliary valve rotor 224 by a spring, to help ensure a fluid-tight seal there between. The ports 1-6 are configured to receive fittings (e.g., standard compression screw/ferrule type fittings) for coupling fluidic tubing to the auxiliary valve stator 222. In some aspects, the auxiliary valve rotor 224 can be rotated to three discrete angular positions, relative to the auxiliary valve stator 222, to connect the rotor grooves 226*a-c* with different ones of the stator ports 1-6 to form different fluidic passageways. One of the grooves, groove 226*a*, includes an extended portion 230 which allows the auxiliary valve rotor 224 to be rotated to a position in which the groove 226*a* forms a fluidic pathway between stator ports 4 and 5, while ports 1-3 and 6 are dead ended.

Also by way of illustration, the inject valve 240 is another six-port rotary shear valve that includes an inject valve stator 242 having a plurality of ports, numbered 1' through 6' in FIG. 2, and an inject valve rotor 244. The inject valve rotor 244 has a rotor interface, which includes three fluid conduits in the form of arcuate grooves 246*a-c*. When assembled, the rotor interface is urged into contact with the inject valve stator 242, e.g., by pressure exerted on the inject valve rotor 244 by a spring, to help ensure a fluid-tight seal there between. The ports 1'-6' are configured to receive fittings (e.g., standard compression screw/ferrule type fittings) for coupling fluidic tubing to the inject valve stator 242. Port 1' is fluidically connected to port 4' via a sample loop 248 (e.g., fluidic tubing external to the inject valve stator 242). Port 2' is fluidically connected to a metering syringe 250 and port 3' is connected to a needle 252. The metering syringe 250 and needle 252 are disposed within the sample manager 170 and are operable to aspirate sample from vials 254 also in the sample manager 170. Port 5' of the inject valve 240 is connected to port 4 of the auxiliary valve 220, and port 6' of the inject valve 240 is connected to port 1 of the auxiliary valve 220. The connections between port 2' and the syringe 250, between port 3' and the needle 252, between port 5' and port 4, and between port 6' and port 1 are made via the fluidic tubing 260*a-d*.

Also by way of illustration, the inject valve rotor 244 can be rotated to two discrete angular positions, relative to the inject valve stator 242, to connect the rotor grooves 246*a-c* with different ones of the stator ports 1'-6' to form different fluid passageways.

In some aspects, the pressure at the exit of the system, as controlled by the automated backpressure regulator (ABPR) in the $CO_2$-based system of the subject technology is from about 1000 psi to about 9000 psi, or any pressures there between. In some aspects, the backpressure is any pressure between the range of about 1000 psi to about 6000 psi. In another aspect, the ABPR is set at 1700 psi, 2200 psi, 2500 psi, 2900 psi, 3200 psi, 3500 psi. In one aspect, overall, the ABPR of the $CO_2$-based systems provide steady pressure levels and improved pressure gradients.

In the $CO_2$-based systems, temperature fluctuations in the pumping systems which may result in system pressure fluctuations are also reduced or eliminated. This leads to a reduced baseline noise of chromatograms of the $CO_2$ based system of the subject technology. Alternatively or in addition, the $CO_2$-based systems that can be used in the methods described herein minimize the consumption of mobile phase solvents (e.g. methanol, acetonitrile, etc.) thereby generating less waste for disposal and reducing the cost of analysis (by more than 100 fold, in some cases) per sample.

Exemplary processes for operating the $CO_2$ based systems described herein are described in e.g., U.S. Patent Application Publication Nos. 2015/0331001 and 2014/0157871, each of which are incorporated herein by reference.

Column Chemistries

The solid stationary phase of the chromatography columns of the $CO_2$ based system includes porous inorganic or inorganic/organic hybrid particles with the mechanical stability and structural integrity required to withstand the operating pressures of the system.

Inorganic particles suitable for use in the system and method of the subject technology include e.g., silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In certain aspects, such inorganic particles may have no surface modifications. For example, without surface modifications, silica is characterized by the presence of silanol groups on its surface. In other aspects, the inorganic particles, e.g., silica, may have been surface modified. For example, silica can be surface modified or derivatized with an organic polar or nonpolar functional group such as butyl (C4), octyl (C8), octadecyl (C18), triacontyl (C30), phenyl, amino, cyano, etc. A suitable commercially available column that includes such particles is, for example, the ACQUITY UPC2 HSS C18 SB column from Waters Technologies Corporation, Milford, Mass.

Hybrid particles suitable for use in the system and method of the subject technology include an inorganic portion such as, e.g., alumina, silica, titanium or zirconium oxides, or ceramic material; and an organic portion bonded to one or more atoms of the inorganic portion. Exemplary hybrid materials are disclosed in e.g., U.S. Pat. No. 4,017,528, the contents of which is incorporated herein by reference.

In some aspects, the organic portion of the hybrid particles is a C1-C18 aliphatic or aromatic moieties (which may additionally be substituted with alkyl, aryl, cyano, amino, hydroxyl, diol, nitro, ester, ion exchange or embedded polar functionalities) or a substituted or unsubstituted C1-C18 alkylene, alkenylene, alkynylene or arylene moiety. In one aspect, where the inorganic portion is silica, "hybrid silica" refers to a material having the formula $SiO_2/(R^2_pR^4_qSiO_t)_n$ or $SiO_2/[R^6(R^2_rSiO_t)_m]_n$ (disclosed in U.S. Pat. Nos. 7,919, 177; 7,223,473, and 6,686,035, each of which is hereby incorporated herein by reference) wherein $R^2$ and $R^4$ are independently C1-C18 aliphatic or aromatic moieties (which may additionally be substituted with alkyl, aryl, cyano, amino, hydroxyl, diol, nitro, ester, ion exchange or embedded polar functionalities), $R^6$ is a substituted or unsubstituted C1-C18 alkylene, alkenylene, alkynylene or arylene moiety bonded to one or more silicon atoms or bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, or alternatively, 0.1 to 1, or alternatively 0.2 to 0.5. $R^2$ may be additionally substituted with a functionalizing group R.

The functionalizing group R includes organic functional groups which impart a certain chromatographic functionality to a chromatographic stationary phase, including, e.g., octadecyl (C18) or phenyl. Such functionalizing groups are present in, e.g., surface modifiers such as disclosed herein which are attached to the base material, e.g., via derivatization or coating and later cross slinking, imparting the chemical character of the surface modifier to the base material. In one aspect, such surface modifiers have the formula $Z_a(R')_bSi-R$, where Z=Cl, Br, I, C1-C5 alkoxy, dialkylamino, e.g., dimethylamino, or trifluoromethanesulfonate; a and b are each an integer from 0 to 3 provided that a+b=3; R' is a C1-C6 straight, cyclic or branched alkyl group, and R is a functionalizing group. R' may be, e.g., methyl, ethyl, propyl, isopropyl, butyl, t-butyl, secbutyl, pentyl, isopentyl, hexyl or cyclohexyl. In one aspect, R' is methyl.

The porous inorganic/organic hybrid particles possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later crosslinking, imparting the chemical character of the surface modifier to the base material. In one aspect, the organic groups of the hybrid particle react to form an organic covalent bond with a surface modifier. The surface modifiers can form an organic covalent bond to the particle's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds.

In one aspect, the solid stationary phase of the chromatography columns herein include a monolith, particles, porous particles, and/or superficially porous particles. Particles can be spherical or non-spherical. The solid stationary phase can include silica, inorganic silica, and/or metal oxide. In one aspect, the column is equipped with one or more frits to contain the stationary phase material. In aspects in which the stationary phase material is monolithic, the housing may be used without the inclusion of one or more frits.

The solid stationary phase includes, for example, particles having a mean size within the range of about 0.5-3.5 microns, though a smaller or larger size could be selected if appropriate for a desired application. In one aspect, the mean particle size is 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 or 3.5 microns. In general, particle size can be selected in view of the desired pressure and/or flow rate. For example, larger particle size can be used to achieve consistent pressure from a column head to an end during high pressurized digestion. Alternatively, smaller particle sizes result in higher flow rates and higher efficiency, which yield faster and more sensitive separations. The solid stationary phase can include pores having a mean pore volume within the range of 0.1-2.5 cm/g. In one aspect, the mean pore volume is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 cm/g. In some aspects, porous particles may be advantageous because they provide a relatively large surface area (per unit mass or column volume) for protein coverage at the same time as the ability to withstand high pressure.

The solid stationary phase can include pores having a mean pore diameter within the range of 100-1000 Angstroms. For example, in some aspects, the mean pore diameter of the solid stationary phase particles is about 100, 200, 300, 400, 500, 600, 700, 800, 900, 1000 Angstroms, or any value or range there between.

In one aspect, the chromatography or separation column herein includes (a) a column having a cylindrical interior for accepting a packing material, and (b) a packed chromatographic bed comprising a porous material comprising an organosiloxane/$SiO_2$ material having the formula $SiO_2/(R^2_p R^4_q SiO_t)n$ or $SiO_2/[R^6(R^2_r SiO_t)_m]_n$, as described above, wherein $R^2$ and $R^4$ are independently C1-C18 aliphatic, styryl, vinyl, propanol, or aromatic moieties, $R^6$ is a substituted or unsubstituted C1-C18 alkylene, alkenylene, alkynylene or arylene moiety bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, said porous hybrid silica chromatographic matrix having a chromatographically-enhancing pore geometry and average pore diameters of about 100 to 300 A. In one aspect, the porous particles of hybrid silica have been surface modified. In another aspect, the particles have been surface modified by a surface modifier selected from the group consisting of an organic group surface modifier, a silanol group surface modifier, a polymeric coating surface modifier, and combinations thereof. In another aspect, the surface modifier has the formula $Z_a(CR')_b Si$—R, where Z=CI, Br, I, C1-05 alkoxy, dialkylamino or trifluoromethanesulfonate; a and b are each an integer from 0 to 3 provided that a+b=3; R' is a C1-C6 straight, cyclic or branched alkyl group, and R is a functionalizing group.

The functionalizing group R may include alkyl, alkenyl, alkynyl, aryl, cyano, ammo, diol, nitro, cation or anion exchange groups, or alkyl or aryl groups with embedded polar functionalities. Examples of suitable R functionalizing groups include C1-C30 alkyl, including C1-C20, such as octyl (C8), octadecyl (C18), and triacontyl (C30); alkaryl, e.g., C1-C4-phenyl; cyanoalkyl groups, e.g., cyanopropyl; diol groups, e.g., propyldiol; amino groups, e.g., aminopropyl; and alkyl or aryl groups with embedded polar functionalities, e.g., carbamate functionalities such as disclosed in U.S. Pat. No. 5,374,755, the contents of which is incorporated herein by reference. In one aspect, the surface modifier is an organotrihalosilane, such as octyltrichlorosilane or octadecyltrichlorosilane. In another aspect, the surface modifier may be a halopolyorganosilane, such as octyldimethylchlorosilane or octadecyldimethylchloro silane.

In one aspect, the hybrid particle's organic groups and silanol groups are both surface modified or derivatized. In another aspect, the particles are surface modified by coating with a polymer. In certain aspects, surface modification by coating with a polymer is used in conjunction with silanol group modification, organic group modification, or both silanol and organic group modification.

Polymer coatings are known in the literature and may be provided generally by polymerization or polycondensation of physisorbed monomers onto the surface without chemical bonding of the polymer layer to the support (type I), polymerization or polycondensation of physisorbed monomers onto the surface with chemical bonding of the polymer layer to the support (type II), immobilization of physisorbed prepolymers to the support (type III), and chemisorption of pre synthesized polymers onto the surface of the support (type IV). See, e.g., Hanson et al., J. Chromat. A656 (1993) 369-380, the contents of which is incorporated herein by reference. As noted above, coating the hybrid material with a polymer may be used in conjunction with various surface modifications described in U.S. Pat. Nos. 7,919,177; 7,223,473, and 6,686,035, each of which are incorporated herein by reference. Additional inorganic/organic hybrid particles are disclosed in e.g., WO 2010/141426, which is hereby incorporated herein by reference.

Exemplary commercially available columns that include such inorganic/organic hybrid particles suitable for the methods described herein include, for example, the ACQUITY UPC2 ethylene bridged hybrid (BEH), BEH 2-EP, and charged surface hybrid (CSH) C18 SB columns from Waters Technologies Corporation, Milford, Mass.

In a ninth exemplary embodiment, the chromatography columns used in the methods described herein comprise hybrid particles. Additional features are described herein such as e.g., those described in the first, second, third, fourth, fifth, sixth, seventh, and eighth exemplary embodiments.

In a tenth exemplary embodiment, the chromatography columns used in the methods described herein comprise hybrid particles having an average particle size of 1.7 or 3.5 um. Additional features are described herein such as e.g., those described in the first, second, third, fourth, fifth, sixth, seventh, eighth, and ninth exemplary embodiments.

In an eleventh exemplary embodiment, the chromatography columns used in the methods described herein comprise hybrid particles having an average particle size of 1.7 or 3.5 urn, and wherein the hybrid particles are surface modified. Additional features are described herein such as e.g., those described in the first, second, third, fourth, fifth, sixth, seventh, eighth, ninth, and tenth exemplary embodiments.

In a twelfth embodiment, the chromatography column used in the methods described herein comprise hybrid particles that are surface modified with fluorophenyl groups or diethylamine groups. Additional features are described herein such as e.g., those described in the first, second, third, fourth, fifth, sixth, seventh, eighth, ninth, tenth, and eleventh exemplary embodiments.

In a thirteenth embodiment, the chromatography column used in the methods described herein comprise hybrid particles having an average pore size of 130 Å. Additional features are described herein such as e.g., those described in the first, second, third, fourth, fifth, sixth, seventh, eighth, ninth, tenth, eleventh, or twelfth exemplary embodiments.

In a fourteenth exemplary embodiment, the particles used in the chromatography columns of the methods described herein have the following specifications:

| Chemistry | Particle Shape | Particle Size (um) | Pore Size (Å) | Surface Area (m²/g) |
|---|---|---|---|---|
| Exemplified Column 1: Hybrid particles with phenyl surface modification/polymer | Spherical | 1.7, 3.5 | 135 | 185 |

-continued

| Chemistry | Particle Shape | Particle Size (um) | Pore Size (Å) | Surface Area (m$^2$/g) |
|---|---|---|---|---|
| coating (e.g., CSH fluorophenyl, Waters Technologies Corporation, Milford, MA) | | | | |
| Exemplified Column 2: Hybrid particles with diethylamine surface modification/polymer coating (e.g., Torus DEA, Waters Technologies Corporation, Milford, MA) | Spherical | 1.7 | 130 | 185 |

Additional features are described herein such as e.g., those described in the first, second, third, fourth, fifth, sixth, seventh, eighth, ninth, tenth, eleventh, twelfth, or thirteenth exemplary embodiments.

In one aspect, the internal diameter (ID) of the chromatography column in the methods described herein is about 1 mm to 5 mm, or 2 mm to 4 mm, or 2.0 mm to 2.5 mm. In one aspect, the ID of the column is about 2.1 mm. In some aspects, the length of the chromatography column is 30 mm to 200 mm or 50 mm to 150 mm. In one aspect, the length of the chromatography column is about 50 mm. In one aspect, the length of the chromatography column is about 100 mm. In another aspect, the length of the chromatography column is about 150 mm.

In one aspect, depending on the column dimension chosen and optimization necessary, the flow rate of the mobile phase is set between about 0.1 mL/min to 4 mL/min, or any intervals there between, e.g., 0.5 mL/min to 3.5 mL/min, or at 1.0 mL/min, with a backpressure regulator setting of about 1000-9000 psi or about 2000-8000 psi, or about 3000-6000 psi, or about 4000-5000 psi. In other aspects, the temperature at which the chromatography column operates is adjusted to a practical working range of about 5° C. to 85° C., or any specific temperature within this range. In some aspects, the column compartment temperature ranges from about 20° C. to 70° C.

Kits and Computer Mediums

Kits for quantifying ondansetron and related impurities by the $CO_2$-based chromatography methods and apparatus described herein are also provided. In one embodiment, a kit may comprise a first known quantity of a first calibrator, a second known quantity of a second calibrator, and optionally comprising ondansetron and related impurities, wherein the first known quantity and the second known quantity are different, and wherein the first calibrator, the second calibrator, and the ondansetron and related impurities are each distinguishable in a single sample by mass spectrometry.

The kits described herein may also comprise instructions for: (i) obtaining a mass spectrometer signal comprising a first calibrator signal, a second calibrator signal, and ondansetron and related impurities from the single sample comprising the first known quantity of the first calibrator, the second known quantity of the second calibrator, and optionally comprising ondansetron and related impurities; and (ii) quantifying ondansetron and related impurities in the single sample using the first calibrator signal, the second calibrator signal, and the signal of the one or more fatty acids.

Computer readable mediums for use with the $CO_2$-based chromatography methods and apparatus are also provided. In an exemplary embodiment, a computer readable medium may comprise computer executable instructions adapted to: separating ondansetron and related impurities as described herein and obtaining a mass spectrometer signal comprising a first known quantity of a first calibrator, a second known quantity of a second calibrator, and optionally comprising ondansetron and related impurities, wherein the first known quantity and the second known quantity are different, and wherein the first calibrator, the second calibrator, and the ondansetron and related impurities are each distinguishable in a single sample by mass spectrometry.

The computer readable medium may further comprise executable instructions adapted to quantifying ondansetron and related impurities in the single sample using the first calibrator signal, the second calibrator signal, and the signal of the ondansetron and related impurities.

The subject technology is further illustrated by the following examples which should not be construed as limiting. The contents of all references, patents and published patent applications cited throughout this application, are incorporated herein by reference.

EXEMPLIFICATION

Separation of Ondansetron and Related Impurities

Ondansetron and related impurities A, C, D, E, F, and G were purchased from Sigma Aldrich (catalog numbers 1478582, 43924, 42243, 54318, 02739, 02736, 92318 respectively). Ondansetron impurities B and H were purchased from TLC Pharmaceutical Standards (catalog numbers O-038 and O-039 respectively). All 9 compounds were weighed and dissolved in the appropriate amount of methanol to afford separate stock solutions at a concentration of 1 mg/mL.

10 μL of each stock solution was combined with 430 μL of isopropanol to afford a solution with a final concentration for all compounds of 20 μg/mL. 2 μL of the combined sample was injected into the $CO_2$-based chromatography system for analysis with the following conditions.

Mobile phase A: $CO_2$
Mobile phase B: 0.2% (v/v) $NH_4OH$ in Methanol
Chromatographic Column: Exemplified Column 2, 1.7 um, 3×100 mm (Torus DEA, Waters Technologies Corporation, Milford, Mass.)
Mobile phase A: $CO_2$
Mobile phase B: 0.2% (v/v) $NH_4OH$ in Methanol
LC Flow Rate: 1 mL/min
LC Gradient:

| Time | % A | % B | Curve |
|---|---|---|---|
| 0.0 | 95 | 5 | — |
| 3.5 | 85 | 15 | 6 |
| 4.5 | 75 | 25 | 6 |
| 6.5 | 75 | 25 | 1 |
| 8.0 | 95 | 5 | 1 |

Figure 6:
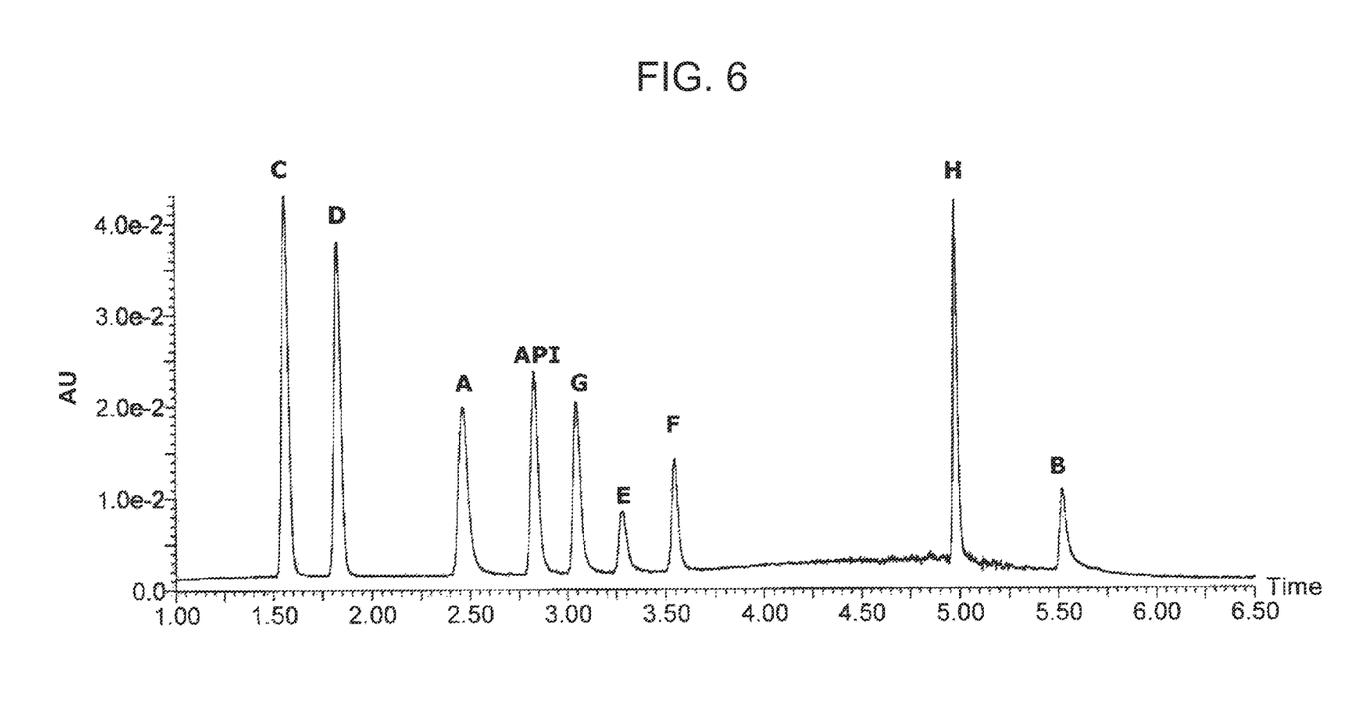
FIG. 6 depicts a chromatogram of the separation of ondansetron and all related impurities using a diethylamine based chromatography column following the $CO_2$-based chromatography methods described herein.

Column Temperature: 30° C.
ABPR: 4000 psi
Detection: 212 nm—compensated 310-410 nm
Data Collection Rate: 10 Hz The results from this separation are shown in FIG. 6. API refers to Ondansetron, and A-H refer to Impurity A-Impurity H.

Alternative Separation of Ondansetron and Related Impurities A, C, D, E, F, and G Ondansetron and related impurities A, C, D, E, F, and G were purchased from commercial sources. All 7 compounds were weighed and dissolved in the appropriate amount of methanol to afford separate stock solutions at a concentration of 1 mg/mL.

10 μL of each stock solution was combined with 430 μL of isopropanol to afford a solution with a final concentration for all compounds of 20 μg/mL. 2 μL of the combined sample was injected into the $CO_2$-based chromatography system for analysis with the following conditions.

Method 1
Mobile Phase A: $CO_2$
Mobile Phase B/Co-Solvent (modifier): 0.2% $NH_4OH$ in methanol
Make Up Flow Solvent (modifier): isopropanol
Chromatographic Column: Exemplified Column 1, 1.7 um, 3×100 mm (CSH fluoro-phenyl, Waters Technologies, Milford, Mass.)
LC Flow Rate: 1 mL/min
LC Gradient:

| Time | % A | % B | Curve |
|------|-----|-----|-------|
| 0.0  | 98  | 2   | —     |
| 5.0  | 45  | 55  | 6     |
| 6.5  | 45  | 55  | 1     |
| 8.0  | 98  | 2   | 1     |

Figure 4:
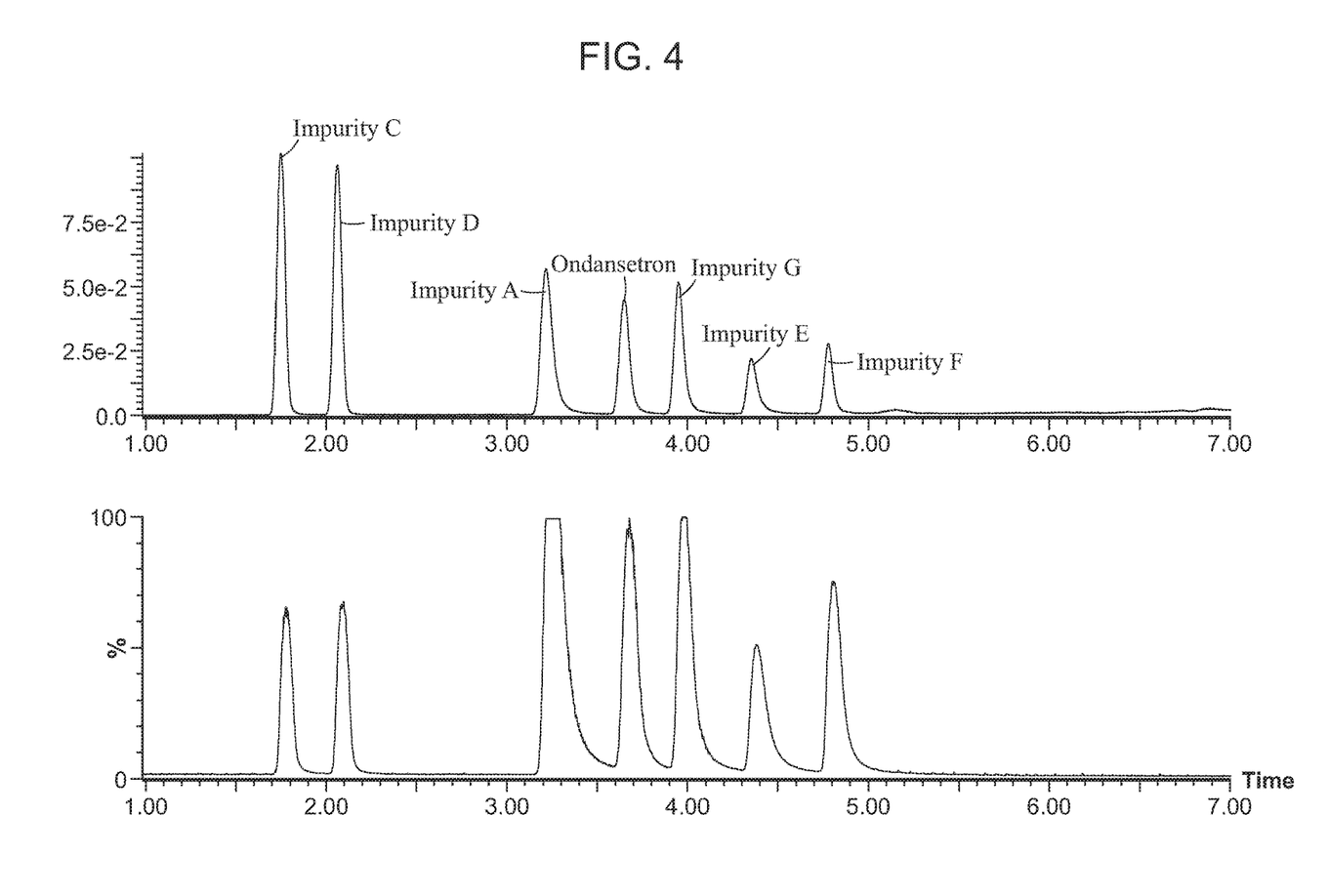
FIG. 4 depicts a chromatogram of the separation of ondansetron and related impurities using a diethylamine based chromatography column following the $CO_2$-based chromatography methods described herein.

Make Up Solvent Flow Rate: 0.3 mL/min
Column Temperature: 30° C.
APBR: 4500 psi
Detection: 216 nm
Data Collection Rate: 20 Hz
The results from method 1 are shown in FIG. 4.

Method 2
Mobile Phase A: $CO_2$
Mobile Phase B/Co-Solvent (modifier): 0.2% $NH_4OH$ in methanol
Make Up Flow Solvent (modifier): isopropanol
Chromatographic Column: Exemplified Column 2, 1.7 um, 3×100 mm (Torus DEA, Waters Technologies Corporation, Milford, Mass.)
LC Flow Rate: 1 mL/min
LC Gradient:

| Time | % A | % B | Curve |
|------|-----|-----|-------|
| 0.0  | 95  | 5   | —     |
| 5.0  | 87  | 13  | 6     |
| 6.5  | 87  | 13  | 1     |
| 8.0  | 95  | 5   | 1     |

Make Up Solvent Flow Rate: 0.3 mL/min
Column Temperature: 30° C.
APBR: 4000 psi
Detection: 216 nm
Data Collection Rate: 20 Hz The results from method 2 are shown in FIG. 4. As seen from both methods, optimal separation is achieved between all 7 compounds using the $CO_2$-based chromatography methods described herein. In particular, optimal separation was realized between highly polar impurities E and F. See e.g., FIG. 3 and FIG. 4, where the difference in retention time is about 15-20 seconds.

Figure 5:
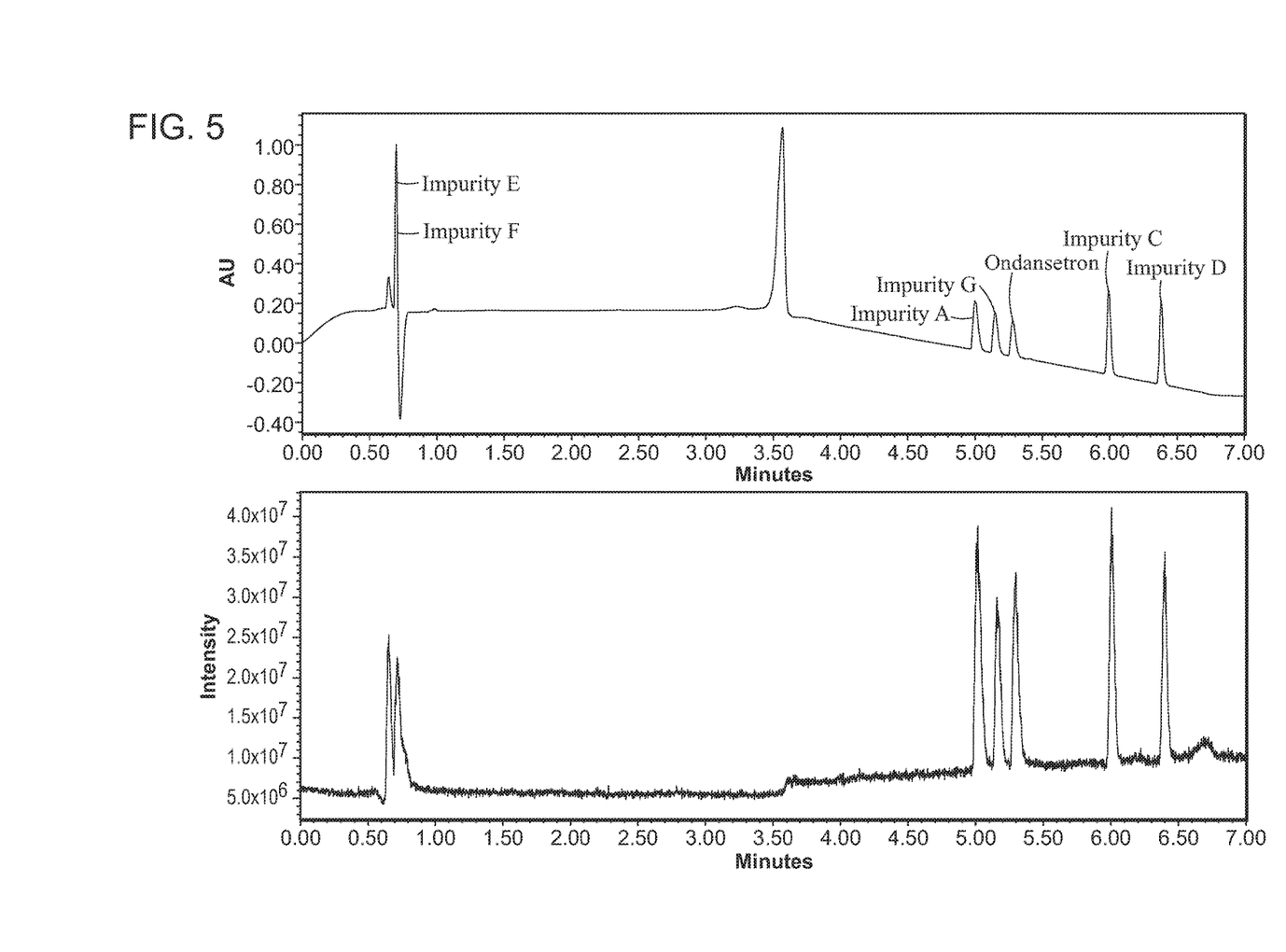
FIG. 5 depicts a chromatogram of an attempted separation of ondansetron and related impurities using traditional reverse phase HPLC methods.

For comparison FIG. 5 shows the results from a reverse-phase HPLC based separation method for Ondansetron and related impurities A, C, D, E, F, and G using 0.1% formic acid in water/acetonitrile. The flow rate was 0.4 mL/min with a 2 min hold at 100% at 0.1% formic acid in water, followed by a gradient to 50% 0.1% formic acid in acetonitrile over 4 min. As shown in FIG. 5, impurities E and F were unretained and elute in the solvent void.

The invention claimed is:

1. A method of separating ondansetron and at least one related impurity using $CO_2$-based chromatography, comprising
applying a sample of ondansetron and at least one related impurity to a chromatography column; and
eluting ondansetron and at least one related impurity from the chromatography column using a mobile phase comprising $CO_2$.

2. The method of claim 1, wherein the mobile phase further comprises a modifier.

3. The method of claim 1, wherein the mobile phase further comprises methanol.

4. The method of claim 1, wherein the related impurities are Impurity E, imidazole, having the structure:

or a salt of hydrate thereof, and Impurity F, 2-methylimidazole, having the structure:

or a salt or hydrate thereof, collectively.

5. The method of claim 1, wherein the related impurities are Impurity E, imidazole, having the structure:

or a salt of hydrate thereof, and Impurity F, 2-methylimidazole, having the structure:

or a salt of hydrate thereof, collectively, and wherein Impurity E and Impurity F have a retention time difference of greater than 10 seconds apart from one another.

6. The method of claim 1, wherein the related impurities are Impurity A, 3-((dimethylamino)methyl)-9-methyl-2,3-dihydro-1H-fluoren-4(9H)-one, having the structure:

or a salt of hydrate thereof, Impurity C, 9-methyl-2,3-dihydro-1H-fluoren-4(9H)-one, having the structure:

or a salt of hydrate thereof, Impurity D, 9-methyl-3-methylene-2,3-dihydro-1H-fluoren-4(9H)-one, having the structure:

or a salt of hydrate thereof, Impurity E, imidazole, having the structure:

or a salt of hydrate thereof, Impurity F, 2-methylimidazole, having the structure:

or a salt of hydrate thereof, and Impurity G, 3-((1H-imidazol-1-yl)methyl)-9-methyl-2,3-dihydro-1H-fluoren-4(9H)-one, having the structure:

or a salt of hydrate thereof, collectively.

7. The method of claim 1, wherein the related impurities are Impurity A, 3-((dimethylamino)methyl)-9-methyl-2,3-dihydro-1H-fluoren-4(9H)-one, having the structure:

or a salt of hydrate thereof, Impurity B, 6,6'-methylenebis(9-methyl-3-((2-methyl-1H-imidazol-1-yl)methyl)-2,3-dihydro-1H-fluoren-4(9H)-one), having the structure:

or a salt of hydrate thereof, Impurity C, 9-methyl-2,3-dihydro-1H-fluoren-4(9H)-one, having the structure:

or a salt of hydrate thereof, Impurity D, 9-methyl-3-methylene-2,3-dihydro-1H-fluoren-4(9H)-one, having the structure:

or a salt of hydrate thereof, Impurity E, imidazole, having the structure:

or a salt of hydrate thereof, Impurity F, 2-methylimidazole, having the structure:

or a salt of hydrate thereof, and Impurity G, 3-((1H-imidazol-1-yl)methyl)-9-methyl-2,3-dihydro-1H-fluoren-4(9H)-one, having the structure:

or a salt of hydrate thereof, and Impurity H, 3-((2-methyl-1H-imidazol-1-yl)methyl)-2,3-dihydro-1H-fluoren-4(9H)-one, having the structure:

or a salt of hydrate thereof, collectively.

8. The method of claim 1, wherein the retention time of the first related impurity eluted from the chromatography column is greater than 1.5 minutes.

9. The method of claim 1, wherein the total elution period of the ondansetron and related impurities is less than 10 minutes.

10. The method of claim 1, wherein the chromatography column comprises hybrid particles.

11. The method of claim 1, wherein the chromatography column comprises hybrid particles having an average particle size of 1.7 or 3.5 um.

12. The method of claim 1, wherein the chromatography column comprises hybrid particles having an average particle size of 1.7 or 3.5 um, and wherein the hybrid particles are surface modified.

13. The method of claim 1, wherein the chromatography column comprises hybrid particles that are surface modified with fluorophenyl groups or diethylamine groups.

14. The method of claim 1, wherein the chromatography column comprises hybrid particles having an average pore size of 130 Å.

* * * * *